United States Patent
Andersson

(10) Patent No.: US 11,904,166 B2
(45) Date of Patent: Feb. 20, 2024

(54) SYSTEMS AND METHOD FOR ADJUSTING AUDITORY PROSTHESES SETTINGS

(71) Applicant: Cochlear Limited, Macquarie University (AU)

(72) Inventor: Marcus Andersson, Mölnlycke (SE)

(73) Assignee: Cochlear Limited, Macquarie University (AU)

( * ) Notice: Subject to any disclaimer, the term of this patent is extended or adjusted under 35 U.S.C. 154(b) by 961 days.

(21) Appl. No.: 16/597,414

(22) Filed: Oct. 9, 2019

(65) Prior Publication Data

US 2020/0112802 A1 Apr. 9, 2020

Related U.S. Application Data

(63) Continuation of application No. 15/009,618, filed on Jan. 28, 2016, now Pat. No. 10,477,325.

(60) Provisional application No. 62/146,013, filed on Apr. 10, 2015.

(51) Int. Cl.
*H04R 25/00* (2006.01)
*A61N 1/36* (2006.01)

(52) U.S. Cl.
CPC ....... *A61N 1/36038* (2017.08); *H04R 25/305* (2013.01); *H04R 25/554* (2013.01); *H04R 25/70* (2013.01); *H04R 2225/39* (2013.01); *H04R 2225/41* (2013.01); *H04R 2225/55* (2013.01)

(58) Field of Classification Search
CPC .............. A61N 1/36038; H04R 25/554; H04R 2225/41; H04R 2225/55; H04R 2225/39; H04R 25/305; H04R 25/70
See application file for complete search history.

(56) References Cited

U.S. PATENT DOCUMENTS

| 7,181,297 B1 | 2/2007 | Pluvinage |
| 10,477,325 B2 | 11/2019 | Andersson |
| 2005/0129262 A1 | 6/2005 | Dillon |
| 2006/0222194 A1* | 10/2006 | Bramslow ............ H04R 25/305 |
| | | 381/314 |

(Continued)

FOREIGN PATENT DOCUMENTS

| CN | 1798452 | 7/2006 |
| CN | 104412618 | 3/2015 |

(Continued)

OTHER PUBLICATIONS

PCT International Search Report and Written Opinion in PCT/IB2016/000618, dated Sep. 8, 2016, 11 pages.

(Continued)

*Primary Examiner* — Christine H Matthews
*Assistant Examiner* — Joshua Daryl D Lannu
(74) *Attorney, Agent, or Firm* — Edell, Shapiro & Finnan, LLC

(57) ABSTRACT

Examples relate to systems and methods for providing settings adjustments to auditory prostheses. One or more settings adjustments can be provided to an auditory device in response to a request for the adjustments or a notification that the recipient is experiencing poor quality. The technologies disclosed herein can dynamically adapt based upon information received from a set of auditory prostheses. The information received from the set of auditory prostheses can be used to update the settings adjustments.

19 Claims, 5 Drawing Sheets

(56) References Cited

U.S. PATENT DOCUMENTS

| | | |
|---|---|---|
| 2010/0111338 A1 | 5/2010 | Ypma |
| 2012/0095528 A1* | 4/2012 | Miller, III .......... A61N 1/37247 |
| | | 607/57 |
| 2012/0183165 A1* | 7/2012 | Foo ....................... H04R 25/50 |
| | | 381/314 |
| 2013/0266165 A1 | 10/2013 | Neumeyer |

FOREIGN PATENT DOCUMENTS

| | | |
|---|---|---|
| CN | 104823463 | 8/2015 |
| EP | 335542 | 12/1994 |
| EP | 1708543 | 10/2006 |
| WO | WO2007042043 | 4/2007 |
| WO | WO2012066149 | 5/2012 |
| WO | 2015024586 A1 | 2/2015 |

OTHER PUBLICATIONS

Office Action in Chinese Application No. 201680021054.3, dated Jun. 4, 2019, 10 pages.

Official Communication in corresponding European Application No. 16 730 886.5-1207, dated Oct. 13, 2021, 17 pages.

\* cited by examiner

SYSTEMS AND METHOD FOR ADJUSTING AUDITORY PROSTHESES SETTINGS

CROSS-REFERENCE TO RELATED APPLICATIONS

This application claims priority as a continuation of U.S. patent application Ser. No. 15/009,618, which issued as U.S. Pat. No. 10,477,325, was filed on Jan. 28, 2016, and claims priority to U.S. Provisional Application No. 62/146,013, which was filed Apr. 10, 2015. Both of these applications are titled "SYSTEMS AND METHOD FOR ADJUSTING AUDITORY PROSTHESES SETTINGS" and are incorporated herein by reference in their entirety for any and all purposes.

BACKGROUND

Hearing loss, which can be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient (i.e., the inner ear of the recipient) to bypass the mechanisms of the middle and outer ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

The technologies disclosed herein relate to systems and methods for providing settings adjustments to auditory prostheses. One or more settings adjustments can be provided to an auditory prosthesis in response to a request for the adjustments or a notification that the recipient desires a settings adjustment. The technologies disclosed herein can dynamically adapt based upon information received from a set of auditory prostheses. The information received from the set of auditory prostheses can be used to update the settings adjustments.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Figure 1:
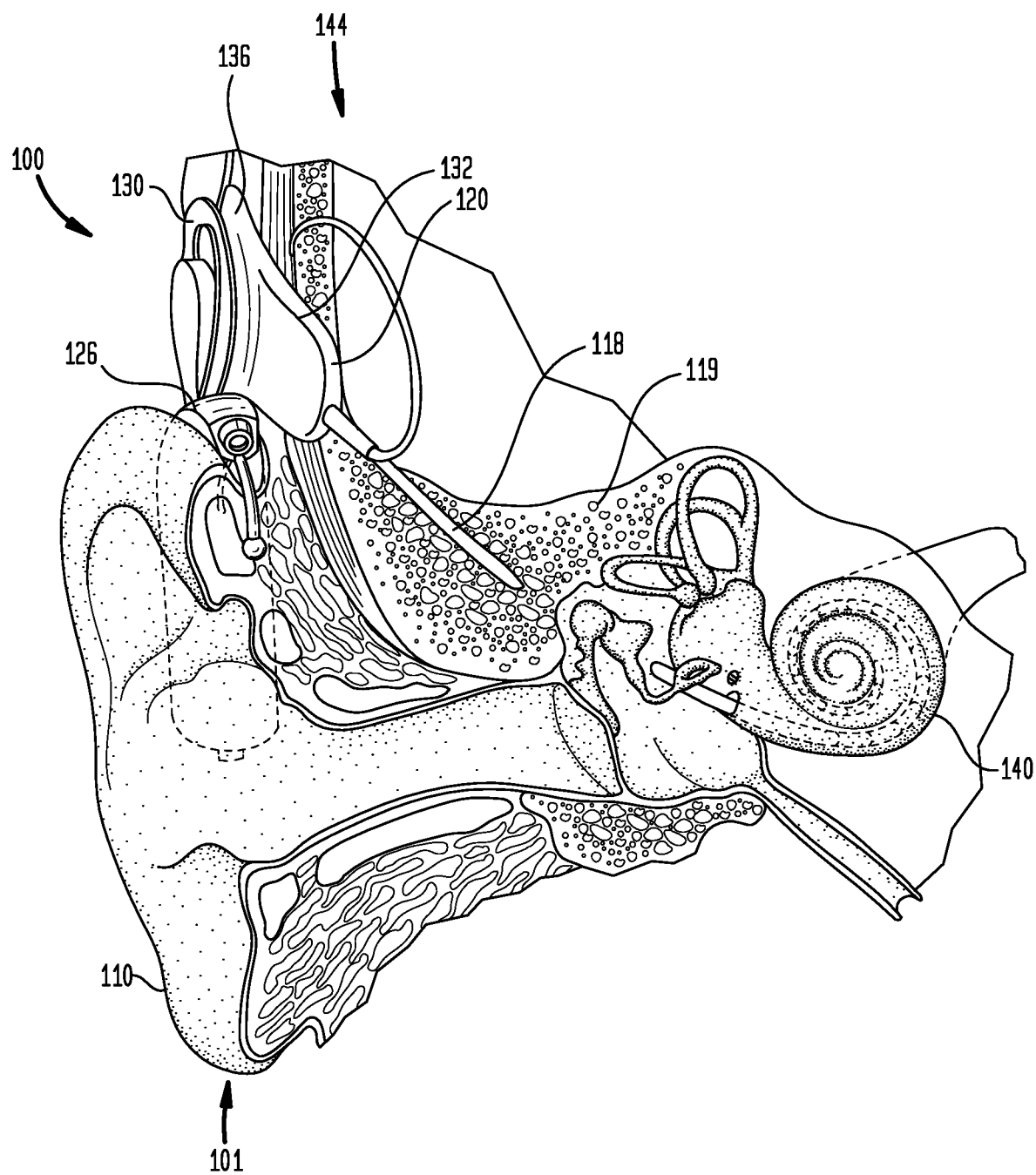
FIG. 1 is a view of a cochlear implant worn on a recipient.

When a recipient first receives an auditory prosthesis, the audio prosthesis is fitted for the user. Fitting the audio prosthesis involves determining settings for the auditory prosthesis which provides the recipient with best hearing experience. The settings adjustments determined during the fitting can be based upon the type of auditory prosthesis, the condition of the recipient, and/or other factors. Due to such differences, the settings adjustments from one recipient to the next can vary. Because of this, the fitting process is often a complex process that is performed by an audiologist with specialized training for a particular auditory prosthesis. Due to the complexity, recipients of auditory prostheses are often not capable of adjusting settings themselves. Furthermore, the optimal settings for an auditory prosthesis can vary from one sound environment to another. For example, the sound characteristics of a concert differ from the sound characteristics of a restaurant. To further exacerbate these problems, incorrect settings could cause a poor experience for the recipient (e.g., distortions, feedback, artifacts, low output, high output, etc.). Often, settings adjustments are required for different sound environments to provide the recipient with an improved experience. Unfortunately, for the difficulties previously described, many recipients are unable to adjust the settings of their auditory prosthesis based upon their current sound environment.

Examples disclosed herein relate to systems and methods that dynamically provide settings for a recipient's auditory prosthesis based upon the current sound environment that the recipient is in. Determining proper settings for a particular sound environment generally requires a significant amount of testing. Furthermore, the settings can differ depending on the type of a user's auditory prosthesis. The systems and methods disclosed herein can modify stored settings adjustment based upon analysis of information from a group of recipients, that is, a number of recipients having a similar audio prosthesis. Settings adjustments can be a set or profile of settings that can be applied by an auditory prosthesis. Settings adjustments can also be one or more instructions to adjust one or more operational parameters of the setting device. While specific examples of settings adjustments have been discussed herein, one of skill in the art will appreciate that other types of settings adjustments can be employed without departing from the spirit of this disclosure. Exemplary settings adjustments can include, but are not limited to, noise reduction management, a compressor system to give the best amplification for signals with loudness close to normal speech, beam forming, and other modifications to stimulation output, sound processing, etc. Additionally, while settings adjustments is referred to in plural form throughout this disclosure, settings adjustments can also be an adjustment or instruction to adjust a single setting.

The technologies disclosed herein relate to systems and methods for performing evolutionary adaption based upon information received from a group of auditory prosthesis recipients. For example, if a subject recipient in a particular sound environment requests setting adjustments, an auditory prosthesis for that recipient can receive an indication of the recipient's poor experience. In response to receiving the indication, the auditory prosthesis can collect or otherwise determine information about the current sound environment. The information about the current sound environment can be sent or associated with a request for a settings adjustment to a remote device (e.g., a server) or a plurality of remote devices (e.g., a distributed network) by the auditory prosthesis or an intermediary device in communication with an auditory prosthesis. In response to transmitting the request, the auditory prosthesis can receive a settings adjustment from the server (or servers). The received settings adjustment can be selected from a plurality of different settings adjustments stored on the remote device. The selection of the received settings adjustment can be based on a priority or ranking such that the higher priority (or higher ranked) settings adjustments are provided to the auditory prosthesis before the lower priority settings adjustments. The received settings adjustment can then be applied to the auditory prosthesis. If the recipient is not satisfied with the settings adjustment, the auditory prosthesis can received another indication of the recipient's desire for new settings and, in turn, send another request for a subsequent settings adjustment. The process can be repeated until the auditory prosthesis is adjusted to the recipient's satisfaction.

The technologies described herein can provide settings adjustments to a large number of recipients of auditory prostheses. The technologies can collect information from each recipient that requests a settings adjustment as well as track whether or not the recipient accepted or rejected a provided settings adjustment. The collected and tracked information can be used to adjust a prioritization of a particular settings adjustment. For example, a prioritization value associated with a particular settings adjustment that has been accepted by many different recipients can be positively modified. Conversely, a prioritization value associated with a particular settings adjustment that has been rejected by many different recipients can be negatively modified. In doing so, a library of settings adjustments can undergo evolutionary adaption such that the better settings adjustments (e.g., settings adjustments that are more frequently accepted by recipients) are initially provided. Over time, a library of settings adjustments can undergo evolutionary adaption as the prioritization values of the different settings adjustments continually change. This allows for the selection of improved settings adjustments over time. Additionally, the technologies described herein are capable of adapting to changes in environment, auditory prostheses, and/or recipient preferences to modify which settings adjustments are selected as circumstances change.

The technologies disclosed herein can be used in conjunction with various types of auditory prostheses, including active transcutaneous bone conduction devices, passive transcutaneous devices, middle ear devices, cochlear implants, and acoustic hearing aids, or other devices acting as an auditory prosthesis. The devices can be wearable (i.e., entirely external to the recipient), partially implanted or totally implantable (either in or on the head, including in specific portions of the anatomy, e.g., in the mouth or below the skin of the skull). Additionally, the technologies can be incorporated into other devices that process sound for a member of a conversation, such as, for example a smartphone, a tablet, a laptop, or other devices. For ease of discussion, the description and examples will be directed to cochlear implants. However, one of skill in the art will appreciate that the technology disclosed herein can be practiced with any type of auditory prosthesis.

FIG. 1 is a view of a cochlear implant 100 worn by a recipient 101. The cochlear implant 100 includes an internal component 144 typically having an internal receiver/transceiver unit 132, a stimulator unit 120, and an elongate stimulating assembly 118. The internal receiver/transceiver unit 132 permits the cochlear implant 100 to receive and/or transmit signals to an external device 126 and includes an internal coil 136, and preferably, a magnet (not shown) fixed relative to the internal coil 136. Internal receiver unit 132 and stimulator unit 120 are hermetically sealed within a biocompatible housing, sometimes collectively referred to as a stimulator/receiver unit. The magnets facilitate the operational alignment of the external and internal coils, enabling internal coil 136 to receive power and stimulation data from external coil 130. Elongate stimulating assembly 118 has a proximal end connected to stimulator unit 120, and a distal end implanted in cochlea 140. Stimulating assembly 118 extends from stimulator unit 120 to cochlea 140 through mastoid bone 119.

In certain examples, external coil 130 transmits electrical signals (e.g., power and stimulation data) to internal coil 136 via a radio frequency (RF) link, as noted above. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 can be positioned in a recess of the temporal bone adjacent auricle 110 of the recipient. Various types of energy transfer, such as infrared (IR), electromagnetic, capacitive and inductive transfer, can be used to transfer the power and/or data from external device to cochlear implant.

Figure 2:
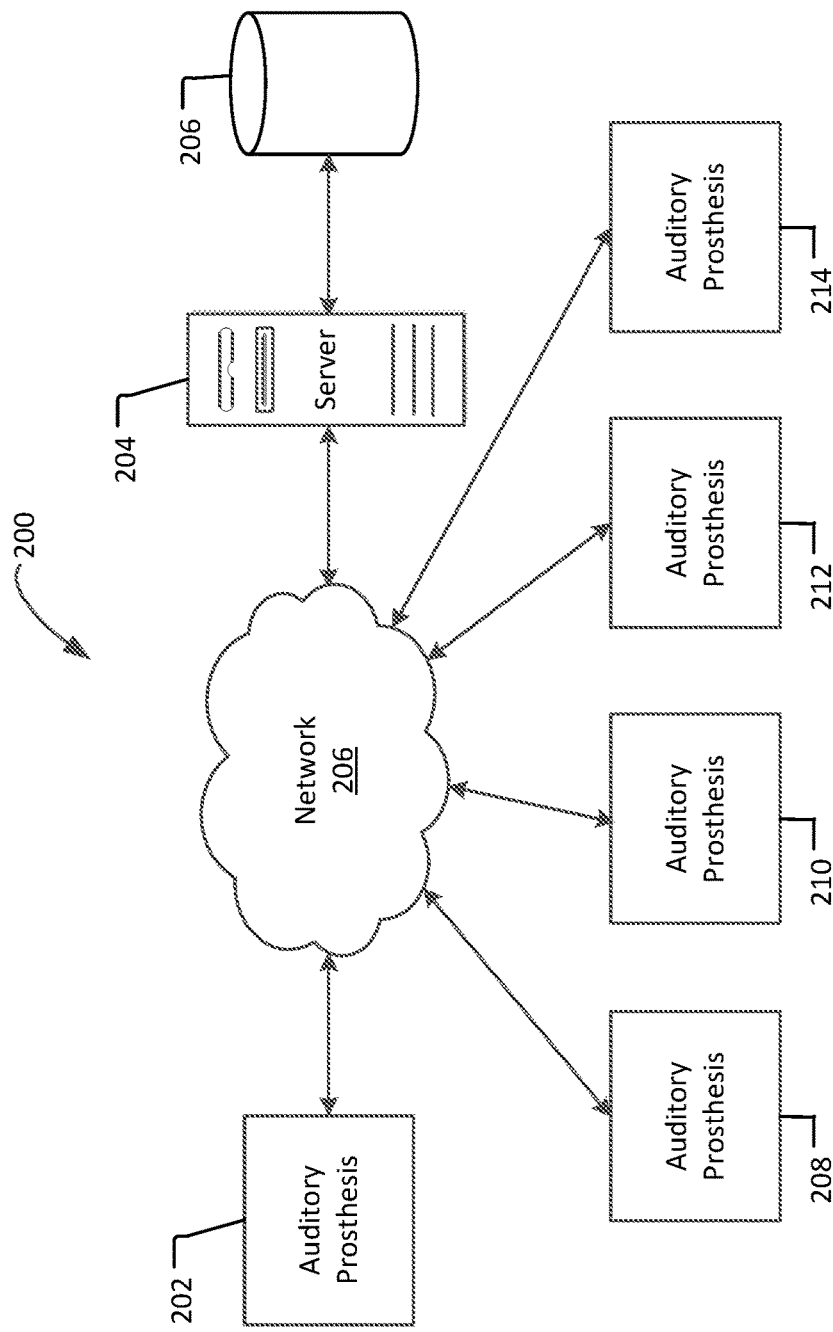
FIG. 2 is an exemplary system for performing evolutionary adaption of settings adjustments for an auditory prosthesis.

FIG. 2 is an exemplary system 200 for performing evolutionary adaption of settings adjustments for an auditory prosthesis. System 200 includes an auditory prosthesis 202 that communicates with a server 204 via a network 206. Although only a single server 204 is illustrated in FIG. 2, one of skill in the art will appreciate that a request for settings adjustments can be sent to a distributed network such as, for example, a cloud computing network. The network 206 can be a wired or wireless network. Although not shown, instead of directly communicating with the server 206, an auditory prosthesis 202 can communicate via an intermediary. For example, the auditory prosthesis 202 can interface with a computing device, such as, for example, a laptop, a tablet computer, a smartphone, etc. The computing device can then communicate with the server 204 via network 206. In examples, auditory prosthesis 202 can receive an indication that the recipient desires a settings adjustment. For example, an indication can be received via a physical interface (e.g., a button) on the auditory prosthesis, can be received via a graphical user interface (GUI) associated with the auditory prosthesis, or via other interfaces (e.g., a speech recognition). In alternate examples, the indication can be automatically generated by the auditory prosthesis. For example, the auditory prosthesis may generate an indication upon detecting a change in its surrounding sound environment. Upon receiving the indication, the auditory prosthesis 202 can send a request to server 206 for settings adjustment. In examples, the request can be provided to the server along with information about the current sound environment. The current sound environment is the sound environment that the auditory prosthesis resides in at the time of receiving the indication. The information about the current sound environment can be collected or otherwise determined by the auditory prosthesis upon receiving the indication. In alternate examples, the information about the current sound environment can be collected prior to receiving the indication. In still further examples, the information collected by the sound environment can be automatically collected and sent to the server 204 without the auditory prosthesis 202 receiving a request for new settings. The information collected about the sound environment can be transmitted to the server at the time that the information is collected or at a later time. In addition to automatically sending information about a sound environment, the auditory prosthesis can send information about itself, such as type of auditory prosthesis, the auditory prosthesis' current settings, etc. Providing information about a sound environment and information about the auditory prosthesis with or without a request for a settings adjustment can be used by the server to prioritize or rank settings. The presence, or lack thereof, of a request for a settings adjustment associated with the information can determine whether the priority or ranking of a settings adjustment is positively or negatively affected. The prioritization or ranking of settings adjustments is discussed in further detail below. The prioritization or ranking can be defined by a value assigned to the settings adjustment (e.g., 1, 2, 3), by the order of the settings adjustments stored in the library (e.g., highest to lowest or lowest to highest), by classification, or by any other method of prioritizing or ranking.

Upon receiving the request from the auditory prosthesis 202, the server 204 determines a settings adjustment. In examples, the determination is based upon information about the current sound environment, the auditory prosthesis type, the recipient's ailment or condition, and/or other information received from the recipient's auditory prosthesis or from other audio prostheses. In examples, the server 204 can be associated with a library of settings adjustments. The library of settings adjustments can be stored on server 204, or on a datastore communicatively coupled to server 204, such as datastore 216. The library of settings adjustments includes settings adjustments that are dynamically determined by the server 206, settings adjustments received from experts (e.g., an audiologist), prior settings provided by the recipient or by other recipients, etc. The settings adjustments resident in the library can be determined based on other types of information departing from the spirit of this disclosure. In examples, the library can be organized according to sound environment, device type, type of hearing loss, age, or other characteristics of a recipient such as the recipient's hobbies (e.g., producing different settings adjustments when playing the drums versus play a flute). The additional information, such as the information about the recipient, can be provided at the time or prior to the time of the request. The information can be provided by the recipient, by an audiologist setting up a profile for the recipient, or by other parties. Upon determining a settings adjustment, the server 204 can transmit the settings adjustment to the auditory prosthesis 202 via network 206.

In examples, the settings adjustment can be prioritized or ranked. For example, a number of different settings adjustments can be stored by the server 204. When the server 204 receives a request for a settings adjustment, it can determine a subset of settings adjustments based upon information associated with the request. For example, there can be subsets of setting adjustments grouped by type of auditory prosthesis (e.g., cochlear implant, traditional hearing aid, bone conduction device, etc.), by recipient status or ailment (e.g., single-sided deafness, sensorineural hearing loss, conductive hearing loss, mixed hearing loss, etc.), by sound environment (e.g., a restaurant, a concert hall, outdoors, etc.), or by any other type of categorization. Different settings adjustments can be prioritized or ranked for each category. The prioritization or ranking can depend upon feedback received from multiple auditory prostheses (e.g., worn by other recipients). For example, server 204 can also receive requests from and provide settings adjustments to auditory prosthesis 208, auditory prosthesis 210, auditory prosthesis 212, and/or auditory prosthesis 214. Auditory prostheses 208-214 can have the same type or different types. In response to providing the settings adjustments, server 204 can receive feedback from auditory prostheses 208-214. Based on the feedback, server 204 can determine the effectiveness of the settings adjustment. For example, if the server 204 receives positive feedback from a number of auditory prostheses 208-214, the ranking or priority of the settings adjustment can be positively modified. Conversely, negative feedback can result in a settings adjustment being negatively adjusted. The priority or ranking of settings adjustments can determine which particular settings adjustment is selected by the server 204. In a further example, the positive and/or negative feedback can be provided with additional information that can be used by the server 204 to develop additional settings adjustments. The library can be updated with the adjusted priority or ranking. In examples where a library is organized into multiple categories, a particular settings adjustment can be included in more than one category. If a particular settings adjustment is included in more than one category, the settings adjustment can be associated with different priority or rankings for each category in which it is included.

Figure 3:
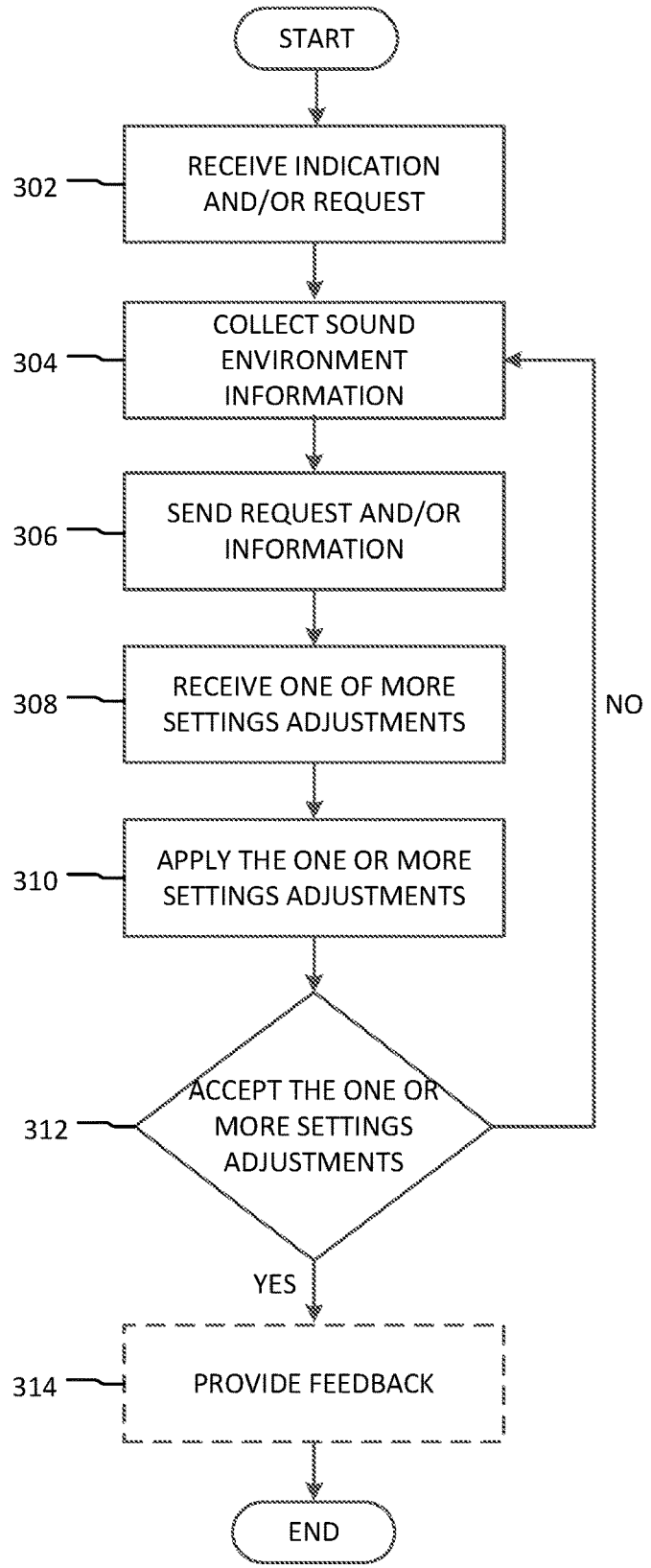
FIG. 3 is an exemplary method for dynamically requesting and applying one or more settings adjustments.

FIG. 3 is an exemplary method 300 for dynamically requesting and applying one or more settings adjustments. The method 300 can be performed by an auditory prosthesis, such as, for example, a cochlear implant, a traditional hearing aid, a bone conduction device, etc. Alternatively, the method 300 can be performed by a computing device connected to or associated with an auditory prosthesis such as a laptop, a smart phone, etc. The operations of the method 300 can be performed by hardware, by software, or by a combination of hardware and software. Flow begins at operation 302 where an indication that a recipient desires a settings adjustment is received. In example, the indication can be received via a user interacting with an interface, such as, for example, a button on an auditory prosthesis, a graphical user interface (GUI) of a computing device, or an auditory command interpreted by a speech recognition component.

In response to receiving the indication or request, flow continues to operation 304 where information about the current sound environment is collected. Collecting information about the current sound environment can include, but is not limited to, performing operations such as such as identifying the presence of wind, identifying the presence of additional speakers and/or the loudness of surrounding speech, autocorrelation of the environment, identifying tonality, performing logPowerSpectrum, identifying spectral jaggedness, detecting distortion, timbre, duration of sounds, phase of sounds, and/or signal to noise ratio (SNR), determining a zero-crossing rate, determining a minima/maxima of periodogram, determining reverberation, determining whether the hearing prosthesis has registered feedback, and/or receiving user inputted data about the sound environment. Collecting information about the current sound environment can also include making a short recording of the current sound environment. The short recording can then be analyzed by the hearing prosthesis or by a remote device. It is contemplated that other methods can be employed to collect information about the sound environment. Any type of information about the sound environment that can be used to determine a settings adjustment can be collected at operation 304.

Flow continues to operation 306 where a request for a settings adjustment is sent to a remote device. An exemplary remote device can be a server. Alternatively, the request can be sent to a distributed network consisting of multiple servers and/or datastores. In one example, the request is sent by itself. In alternate examples, the request can be sent with information about the current sound environment and/or information about an auditory prosthesis. In one example, the request and/or the additional information can be transmitted to a remote device by the auditory prosthesis. For example, the auditory prosthesis can include a wireless interface, such as, for example, a WiFi or Bluetooth interface. In alternate example, the request and/or information can be routed through an intermediary device connected to an auditory prosthesis, such as a smartphone, a tablet, a laptop, and so forth. The intermediary device can be connected to the auditory prosthesis using a wired or wireless connection.

In response to sending the request and/or additional information, flow continues to operation 308 where one or more settings adjustments are received. The one or more settings adjustments can be a profile of settings that can be applied. Settings adjustments can also be one or more instructions to adjust one or more operational parameters of the device. Exemplary settings adjustments can include, but are not limited to, noise reduction management, a compressor system to give the best amplification for signals with loudness close to normal speech, beam forming, and other modifications to stimulation output, sound processing, modifying the aggressiveness of a feedback manager, applying wind noise reduction, etc. In one example, the one or more settings adjustment can be received directly by the auditory prosthesis, for example, in instances where the auditory prosthesis generating the request for settings adjustments has an interface to a network. In other examples, the one or more settings adjustments can be received via an intermediary device that is connected to a network, such as, for example, a smartphone, a tablet, a laptop, or other network connected computing devices. In such examples, the intermediary device can process or modify the one or more settings adjustments prior to providing the one or more settings adjustments to an auditory prosthesis. Upon receiving the one or more settings adjustments, flow continues to operation 310 where the one or more settings adjustments are applied to the auditory prosthesis. For example, the one or more settings adjustments can be used to adjust the configuration settings and/or operation of an auditory prosthesis at operation 310. In one example, the one or more settings adjustments can be automatically applied. In alternate examples, a physical interface or a GUI can be used to provide information to the recipient about the one or more settings adjustments. In such examples, the one or more settings adjustments are not applied unless an acceptance of the one or more settings adjustments is received via the physical interface or GUI.

Flow continues to decision operation 312 where a determination is made as to whether or not the recipient accepts the one or more settings adjustments. In one example, an indication or acceptance can be received via an interface, such as a physical interface (e.g., a button on the auditory prosthesis) or a GUI. In another example, if input has not been received from the user within a predefined window of time, a determination can be made that the user accepts the one or more settings adjustments. If the determination is made that the received settings adjustment is accepted, then flow branches YES to optional operation 314. At optional operation 314, feedback information is sent to the server and/or distributed network that provided the one or more settings adjustment. For example, additional information about the auditory prosthesis, the one or more settings, and/or the sound environment can optionally be provided at operation 314. The additional information provided at operation 314 can be used for the prioritization or ranking or the one more settings adjustments and/or for the creation of new settings adjustments. After providing feedback information at optional operation 314, the method 300 can complete.

Returning to decision operation 312, if a denial of the one or more settings adjustments is received then a determination can be made that the one or more settings adjustments were denied. In alternate examples, a subsequent request for new settings adjustments can also be an indicator that the one or more previously provided settings adjustments were not accepted. If the one or more settings adjustments are not accepted, then flow branches NO and returns to operation 304. Upon returning to operation 304, additional information about the current sound environment can be collected. The method 300 then continues from operation 304. In alternate examples, it is not be necessary to collect additional information about the current sound environment. In such examples, operation 304 can be skipped. Under such circumstances, decision operation 312 can branch NO to operation 306. In further examples, if more than one settings adjustment is received at operation 308, flow can branch NO to operation 308 where another settings adjustment is applied before sending another request to the remote device. In certain embodiments, the method 300 can repeat multiple times until a received settings adjustment is accepted.

Figure 4:
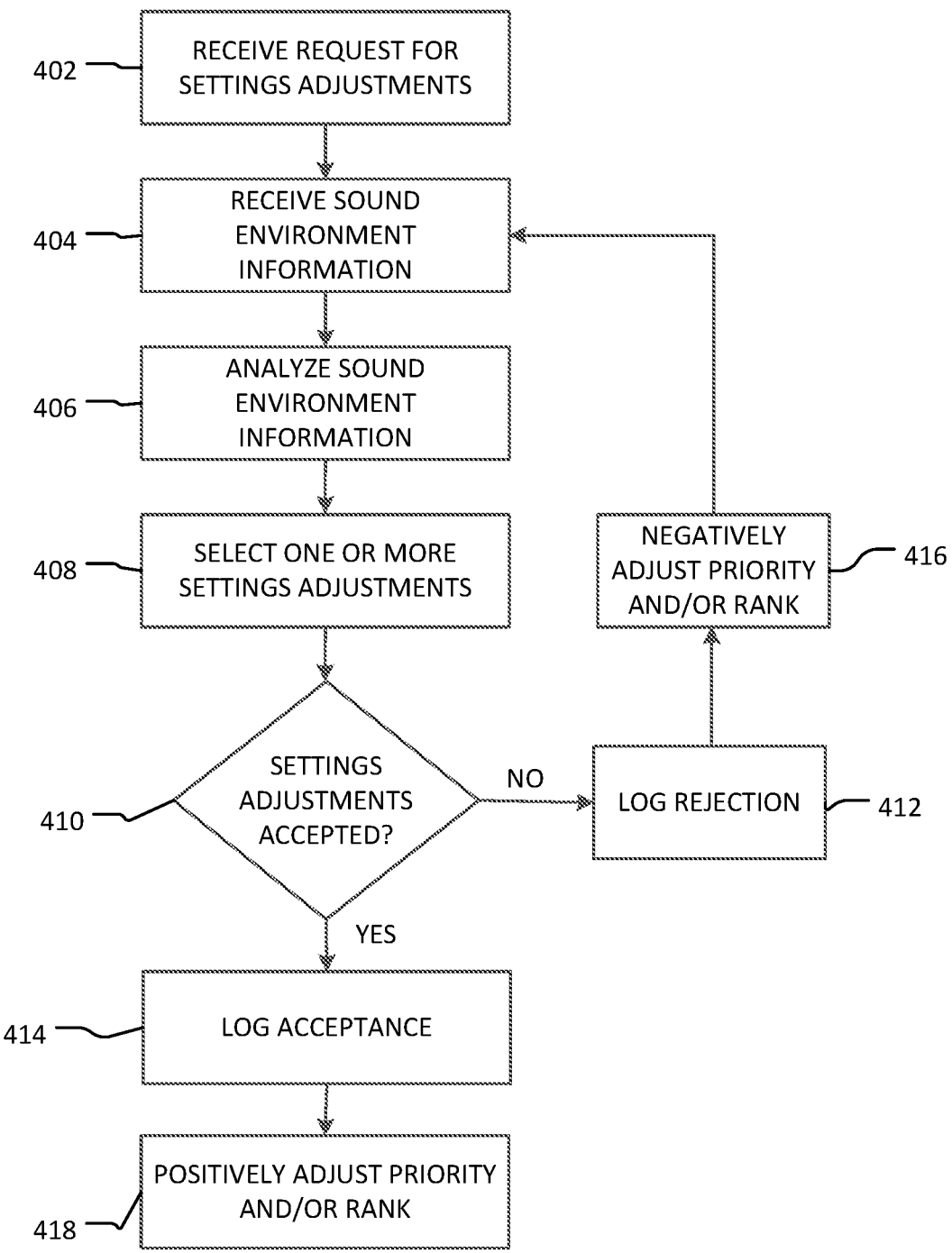
FIG. 4 is an exemplary of a method for providing one or more settings adjustments to an auditory prosthesis.

FIG. 4 is another example of a method 400 for providing one or more settings adjustments to an auditory prosthesis. The method 400 can be performed by a computing device, such as, for example, a server. Alternatively, the method 300 can be performed by multiple computing devices such that one more operations of the method 400 can be performed by different computing devices. For example, the method 400 can be performed by two or more servers that are part of a distributed network. The operations of the method 400 can be performed by hardware, by software, or by a combination of hardware and software. Flow begins at operation 402 where a request for one or more settings adjustments is received. The request can be received from an auditory prosthesis or from an intermediary device communicatively coupled to the auditory prosthesis. In one example, the request is an instruction to provide one or more settings adjustment. Flow continues to operation 404 where additional information is received. The additional information can be received from an auditory prosthesis or from an intermediary device communicatively coupled to the auditory prosthesis. In one example, the additional information can be information about the current sound environment of the auditory prosthesis that needs to be adjusted. In alternate examples, the additional information can relate not to the current sound environment of the auditory prosthesis, but rather to a past sound environment in which the auditory prosthesis was producing poor sound quality and/or a poor user experience. In such examples, the information can be provided not in real-time, but rather at a later time. Receiving past sound environment information can help when prioritizing or ranking different settings adjustments. Other types of information can also be received at operation 404. For example, information about the auditory prosthesis (e.g., type, current settings, model, etc.) and/or information about the recipient can be received in addition to the information about the sound environment. In other example, third party information can also be received. For example, information from an audiologist can also be received at operation 404. While operation 402 is described as receiving information, one of skill in the art will appreciate that such information can be looked up or retrieved from a datastore without departing from the scope of this disclosure.

Flow continues to operation 406 where information about the sound environment is analyzed. In further examples, additional information, such as information about the auditory prosthesis, information about the recipient, and/or third party information, can also be analyzed. For example, analyzing the received data can be used to determine a type or category of settings adjustment. In one example, a fixed ranking of importance can be determined based off of the information about the sound environment. For example, the fixed ranking can give different weights to different characteristics based on importance (e.g., "signal-to-noise ratio" can be weighted relative to "phase of sounds" information based upon a determination that the signal-to-noise ratio is more important when determining a settings adjustment). In another example, the information about the sound environment can be analyzed to determine if there is any significant difference (e.g., higher or lower) of a characteristic as compared to what is considered normal. In such examples, characteristics with significant differences can be prioritized when determining a settings adjustment. In yet another example, a multivariate analysis or principle component analysis can be performed on the information about the sound environment to determine a settings adjustment. While specific types of analysis are described herein, other types of analysis can be performed without departing from the scope of this disclosure. Based upon the analysis, flow continues to operation 408 where one or more settings adjustments are selected and provided to the auditory prosthesis. In example, one or more settings adjustments can be stored in a library, such as the exemplary library described with respect to FIG. 2, that is accessible by the device performing the method 400. The settings adjustments stored in the library can be organized by sound environment, auditory prosthesis type, recipient profiles (e.g., by groups of recipients who have similar preferences or conditions), and/or any other type of information that can be used to categorize a settings adjustment. Furthermore, the one or more settings adjustments stored in the library can be prioritized or ranked such that the settings adjustments with higher priority or rank are selected prior to selecting settings adjustments having a lower priority or rank. Selecting settings adjustments based on priority and/or rank makes it more likely that the selected settings adjustment will be accepted by a recipient of an auditory prosthesis. In such examples, selecting the one or more settings adjustments can include selecting one or more settings adjustments stored in the library.

After providing the one or more settings adjustments to an auditory prosthesis, flow continues to decision operation 410, where it is determined whether or not the recipient accepted the one or more provided settings adjustment. If a subsequent request for settings adjustments is received, or if an indication that the one or more settings adjustments were not accepted, flow branches NO to operation 412 where the rejection of the one or more provided settings adjustments is logged or otherwise stored. In one example, logging the rejection of the one more provided settings adjustments can include recording the one or more provided settings adjustments, the information about the sound environment, information about the auditory prosthesis, third party information, and/or other types of information. Other types of information can include information that relates the one or more provided settings adjustments to a prior selected settings adjustment. That way, if the request received at is a subsequent request for a settings adjustment, a series of requests and rejections can be recorded.

After logging the rejection, flow continues to operation 416 where the prioritization or ranking of the one or more provided settings adjustment are modified. At operation 416, the prioritization or rank of the one or more provided settings adjustments can be negatively affected because the provided settings adjustments were rejected. Negatively affecting the priority or ranking makes it less likely that the one or more settings adjustments will be selected in response to a future request by the same recipient or by a different recipient. Among other benefits, this provides the benefit of making it more likely that an acceptable settings adjustment will be initially selected upon receiving a first request for settings adjustments. As such, the library of settings adjustments can adapt based upon feedback received from an audio prosthesis or an intermediary device. In other examples, a determination can be made about how long a user has been using a provided settings adjustment without requesting another update. In such examples, the longer a recipient keeps the settings can be correlated with user satisfaction, which can result in an adjustment of the priority or ranking of the settings adjustment. In another example, the recipient can be queried to determine a satisfaction level of the settings adjustments. For example, a message can be sent to the recipient to rate the settings adjustment, for example, on a scale, and/or request a written review of the settings adjustments. In such examples, the priority or rankings of the provided settings adjustment can be based on the feedback information from the recipient. In yet another example, multiple setting adjustments can be sent to a recipient for selection. Depending on which settings adjustment is selected by the recipient, the priority or ranking of the different settings adjustments can be modified. Flow then returns to operation 404 where additional information can be collected, if necessary. If it is not necessary to collect additional information, operation 404 can be skipped. Method 400 then repeats.

Returning to decision operation 412, a determination that the one more provided settings adjustment can be made upon receiving an indication that the recipient accepted the one or more provided settings adjustments. Alternatively, the absence of a response from the auditory prosthesis within a predetermined period of time can also indicate that the one or more provided settings adjustments were accepted. If the one or more provided setting adjustments are selected, flow branches YES to operation 414. At operation 414, the acceptance of the one or more provided settings adjustments is logged or otherwise stored. In one example, logging the acceptance of the one more provided settings adjustments can include recording the one or more provided settings adjustments, information about the sound environment, information about the auditory prosthesis, third party information, and/or other types of information. Other types of information can include information that relates the one or more provided settings adjustments to a prior selected settings adjustment. That way, if the request received is a subsequent request for a settings adjustment, a series of requests and rejections that preceded the acceptance can be recorded.

Flow continues to operation 418 where the prioritization or ranking of the one or more provided settings adjustments are positively modified. At operation 418, the prioritization or rank of the one or more provided settings adjustments can be positively modified because the provided settings adjustments were rejected. Positively modifying the priority or ranking makes it more likely that the one or more settings adjustments will be selected in response to a future request by the same recipient or by a different recipient. Among other things, this provides the benefit of making it more likely that an acceptable settings adjustment will be initially selected upon receiving a first request for settings adjustments. As such, the library of settings adjustments can adapt based upon feedback received from an audio prosthesis or an intermediary device. For example, the different techniques previously discussed can be applied at operation 418. The method 400 can then complete.

While operations 416 and 418 are described during execution of the method 400, one of skill in the art will appreciate that the modification or the prioritization or ranking of a settings adjustment can be performed at a later time. For example, the modifications can be performed by a batch process once a day, once a week, etc., rather than in response to receiving a request as described in FIG. 4. In such examples, the logged data can be accessed at a later time and processed to perform the modification. Based on feedback, the library of settings adjustments can be updated periodically or dynamically, thereby leveraging feedback from a large group of users to provide better settings adjustments. In other examples, a short recording (e.g., raw sound output) can be provided to a recipient at a later point. Several different settings adjustments can be applied to the recording. A selection of the best settings adjustment can then be received. Prioritization or ranking can be modified based upon the selection.

Figure 5:
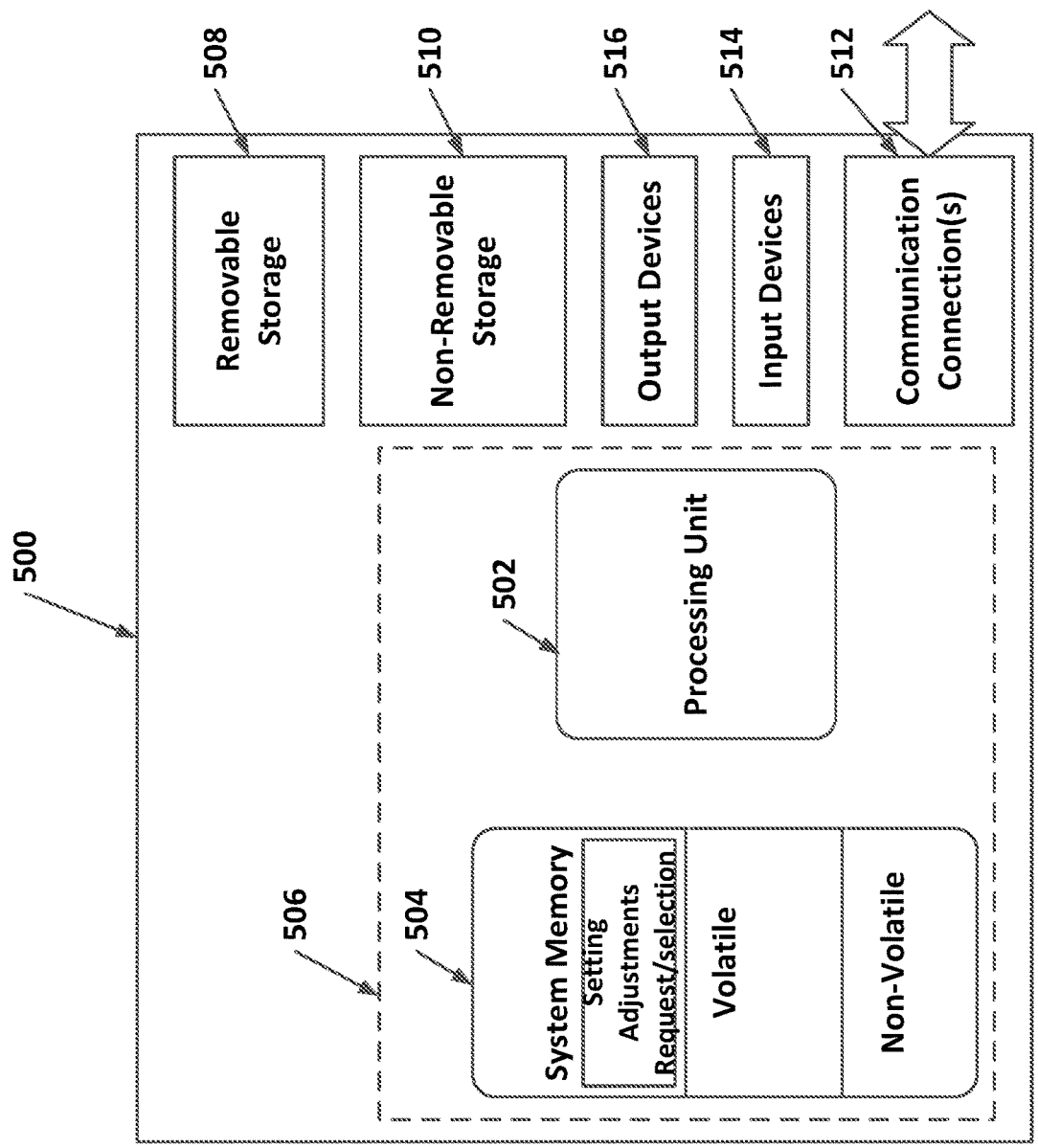
FIG. 5 illustrates one example of a suitable operating environment in which one or more of the present examples can be implemented.

FIG. 5 illustrates one example of a suitable operating environment 500 in which one or more of the present examples can be implemented. This is only one example of a suitable operating environment and is not intended to suggest any limitation as to the scope of use or functionality. Other well-known computing systems, environments, and/or configurations that can be suitable for use include, but are not limited to, auditory prostheses. In embodiments, an auditory prosthesis includes a processing unit and memory, such as processing unit 506 and memory 504. As such, the basic configuration 506 is part of an auditory prosthesis and/or another device working in conjunction with the auditory prosthesis.

In its most basic configuration, operating environment 500 typically includes at least one processing unit 502 and memory 504. Depending on the exact configuration and type of computing device, memory 504 (storing, among other things, instructions to implement and/or perform the functionality disclosed herein) can be volatile (such as RAM), non-volatile (such as ROM, flash memory, etc.), or some combination of the two. This most basic configuration is illustrated in FIG. 5 by dashed line 506. Similarly, environment 500 can also have input device(s) 514 such as a microphone, physical inputs (e.g., buttons), vibration sensors, etc. Other exemplary input device(s) include, but are not limited to, touch screens or elements, dials, switches, voice input, etc. and/or output device(s) 516 such as speakers, stimulation assemblies, etc. Also included in the environment can be one or more communication connections, 512, such as LAN, WAN, point to point, Bluetooth, RF, etc.

Operating environment 500 typically includes at least some form of computer readable media. Computer readable media can be any available media that can be accessed by processing unit 502 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes RAM, ROM, EEPROM, flash memory or other memory technology, solid state storage, or any other tangible or non-transitory medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 500 can be a single device operating in a networked environment using logical connections to one or more remote devices. The remote device can be an auditory prosthesis, a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some examples, the components described herein comprise such modules or instructions executable by operating environment 500 that can be stored on computer storage medium and other non-transitory mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some examples, computer system 500 is part of a network that stores data in remote storage media for use by the computer system 500.

The examples described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some examples of the present technology with reference to the accompanying drawings, in which only some of the possible examples were shown. Other aspects can, however, be embodied in many different forms and should not be construed as limited to the examples set forth herein. Rather, these embodiments were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative embodiments. The scope of the technology is defined by the following claims and any equivalents therein.

What is claimed is:

1. A method comprising:
    receiving information regarding a sound environment in which a hearing device is located;
    based on the information regarding the sound environment, selecting a settings adjustment from a library of a plurality of settings adjustments;
    providing the settings adjustment to the hearing device, wherein operations of the hearing device are modified based on the provided setting adjustment;
    receiving, from the hearing device, a response to providing the settings adjustment; and
    updating a rank of the settings adjustment in the library based on the response received from the hearing device.

2. The method of claim 1, wherein the hearing device is an auditory prosthesis, wherein receiving the information regarding the sound environment includes:
    receiving the information from the auditory prosthesis; and
    wherein providing the settings adjustment includes providing the settings adjustment to the auditory prosthesis.

3. The method of claim 2, wherein the method is performed by a server remote from the auditory prosthesis.

4. The method of claim 2, wherein the method is performed by a computing device directly connected to the auditory prosthesis via a wired or wireless connection.

5. The method of claim 2, further comprising:
    receiving responses from a plurality of auditory prostheses associated with different recipients, wherein the plurality of auditory prostheses include the auditory prosthesis, the responses being associated with one or more settings adjustments of the plurality of settings adjustments; and
    updating the library based on the received responses.

6. The method of claim 1, wherein the plurality of settings adjustments are ranked.

7. The method of claim 1, wherein the response indicates a rejection of the settings adjustment, and wherein the method further comprises:
    providing a different settings adjustment to the hearing device.

8. The method of claim 1, wherein the information regarding the sound environment includes information regarding:
    presence of wind;
    presence of multiple speakers; or
    loudness of surrounding speech.

9. The method of claim 1, wherein the information regarding the sound environment includes recipient-inputted data about the sound environment.

10. The method of claim 1, wherein the settings adjustments includes a setting for noise reduction management, compression, beam forming, or wind noise reduction.

11. A method comprising:
    receiving environment information associated with an environment in which a hearing device is located;
    based on the environment information, selecting a settings adjustment from a library having ranked settings adjustments;
    providing the settings adjustment to the hearing device, wherein operations of the hearing device are modified based on the settings adjustment;
    determining whether a response to the provided settings adjustment has been received from the hearing device; and
    updating a rank of the settings adjustment in the library based on a presence or absence of a response received from the hearing device.

12. The method of claim 11, wherein updating the rank of the settings adjustment in the library based on the presence or the absence of the response includes:
    determining acceptance of the settings adjustment responsive to the absence of a response to the provided settings adjustment within a predetermined amount of time; and
    updating the rank of the settings adjustment in the library based on the acceptance.

13. The method of claim 11, wherein updating the rank of the settings adjustment in the library based on the presence or the absence of the response includes:
    determining acceptance of the settings adjustment responsive to receiving an indication that the settings adjustment was accepted; and
    updating the rank of the settings adjustment in the library based on the acceptance.

14. The method of claim 11, wherein updating the rank of the settings adjustment in the library based on the presence or the absence of the response includes:
    determining rejection of the settings adjustment responsive to receiving an indication that the settings adjustment was rejected; and
    updating the rank of the settings adjustment in the library based on the rejection.

15. The method of claim 11, further comprising:
    receiving an indication of an acceptance of a settings adjustment; and
    logging a series of rejections of settings adjustments that preceded the acceptance of a settings adjustment.

16. A system comprising:
    a datastore storing a library of settings adjustments associated with a plurality of auditory prostheses;
    a computer operating environment comprising:
        one or more processing units; and memory having stored thereon instructions that, when executed by the one or more processing units, causes the one or more processing units to:

provide, to at least one of the plurality of auditory prostheses or a device connected to the at least one of the plurality of auditory prostheses, settings adjustments from the library of settings adjustments;

receive responses from the at least one of the plurality of auditory prostheses or the device connected to the at least one of the plurality of auditory prostheses regarding the provided settings adjustments; and update ranks of the provided settings adjustments in the library of settings adjustments based on the received responses from the at least one of the plurality of auditory prostheses or the device connected to the at least one of the plurality of auditory prostheses.

17. The system of claim 16, wherein updating the ranks of the provided settings adjustments in the library of settings adjustments based on the received responses includes updating ranks of the settings adjustments in the library based on one or more categories associated with the provided settings adjustments.

18. The system of claim 16, wherein the computer operating environment further comprises the datastore.

19. The system of claim 16, further comprising a device configured to:
   collect sound environment information;
   send the sound environment information to the computer operating environment;
   receive a settings adjustment provided by the computer operating environment;
   provide the settings adjustment; and
   accept or reject the provided settings adjustment.

* * * * *